United States Patent [19]

Poenie et al.

[11] Patent Number: 5,576,433
[45] Date of Patent: Nov. 19, 1996

[54] FLUORESCENT CALCIUM INDICATORS TARGETED TO SPECIFIC INTRACELLULAR ENVIRONMENTS

[75] Inventors: Martin F. Poenie; Akwasi Minta, both of Austin, Tex.

[73] Assignee: Texas Fluorescence Laboratories, Inc., Austin, Tex.

[21] Appl. No.: 322,059

[22] Filed: Oct. 12, 1994

[51] Int. Cl.$^6$ ............ C07D 413/14; C07D 413/12; C07D 403/12; C07D 209/20
[52] U.S. Cl. .................... 544/369; 544/373; 548/236; 548/511
[58] Field of Search ............... 544/369; 548/236

[56] References Cited

U.S. PATENT DOCUMENTS

| | | | |
|---|---|---|---|
| 4,603,209 | 7/1986 | Tsien et al. | 548/236 |
| 4,689,432 | 8/1987 | Tsien et al. | 546/255 |
| 5,040,673 | 9/1991 | Tsien et al. | 546/107 |
| 5,134,232 | 7/1992 | Tsien et al. | 540/467 |
| 5,516,911 | 5/1996 | London et al. | 548/236 |

OTHER PUBLICATIONS

DiVirglio et al, *Cell Calcium* 11, p. 57 (1990).
Grynkiewicz et al, *J. Biol. Chem.* 260 p. 3440 (1985).
Hepler et al, *J. Cell. Biol.* 105 p. 2137 (1987).
Hollingworth et al *J. Biophys.* 15, 549a (1987).
Kao et al, *J. Cell. Biol.* 111, p. 183 (1990).
Poenie, *Intracellular Messengers* 20, pp. 1–43 (1992).
Richie et al, *Dev. Immunology* p. 255 (1991).
Tsien, *Biochemistry* 19 p. 2396 (1980).
Tsien, *Nature* p. 527 (1981).
Tsien et al, *Cell Calcium* pp. 145–157 (1985).

*Primary Examiner*—Emily Bernhardt
*Attorney, Agent, or Firm*—Joseph F. Long

[57] ABSTRACT

The present invention discloses several new calcium indicator dyes which are retained in the cytosol or which bind to cellular membranes and report calcium levels near the membrane. These indicators are analogs of a previously described tetracarboxylate calcium indicator fura-2 and indo-1 where the 5' methyl of the BAPTA moiety is replaced with a derivative of propionic acid in the form of —$CH_2CH_2CON$—$(CH2)_n$—$N(X_1)X_2$, where n is 4. The propionic acid derivative provides a flexible means for introducing additional functionality to the calcium indicator without greatly impacting the fluorescence and ion chelating properties of the parental indicator. When $X_1$ is $CH_2COOH$ and $X_2$ is part of a ring system like piperazine, a fluorescent calcium indicator, Fura-PE3, is obtained which resists compartmentalization and leakage out of the cytosol. The tertiary amino group survives subsequent acetoxymethyl esterification of the hexacarboxylate form of the indicator without quaternization. In addition, the tertiary amino group can ionize once the indicator is inside the cell giving a zwitterion. All the zwitterionic calcium indicators reported herein resist leakage and compartmentalization. When $X_1$ is a sufficiently hydrophobic alkyl chain, as in $C_{12}H_{25}$, and $X_2$ is part of a ring system like piperazine, FFP-18, the resulting indicator binds to membranes and reports calcium levels near the membranes.

3 Claims, 11 Drawing Sheets

Titration of PE3 with $Ca^{2+}$ at 20°C, pH 7.2

Titration of PE3 with $Mg^{2+}$

Rates of indicator leakage as determined by the degree of fluorescence quench after adding $Ni^{2+}$ to the extracellular media.
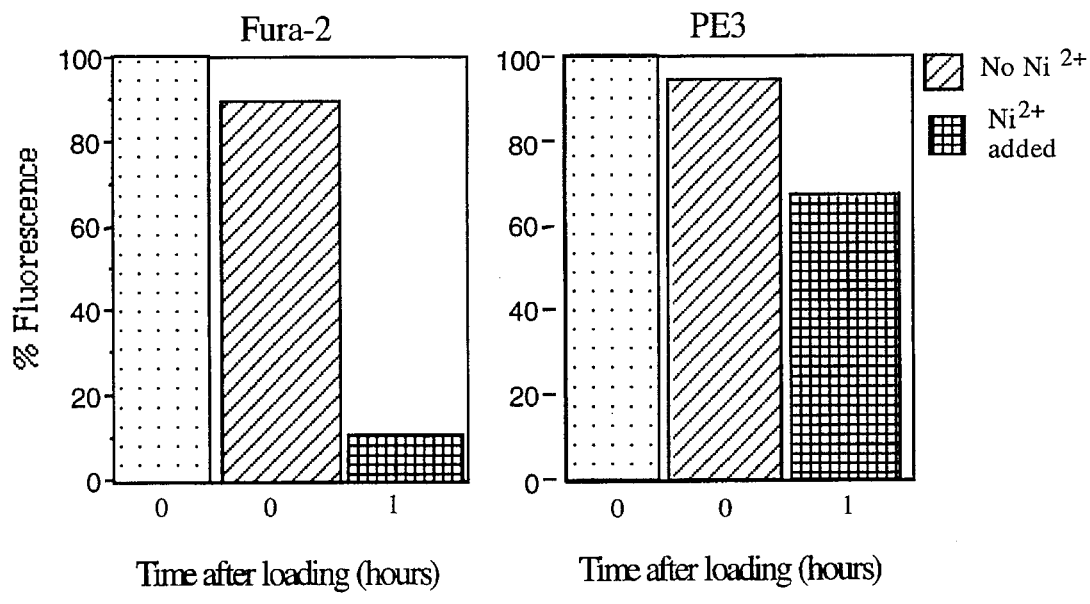
Figure 7
Figure 7A
Drift in apparent baseline $[Ca2+]i$ due to leakage of indicator from fura-2 or PE3 loaded 322 T lymphoma cells.
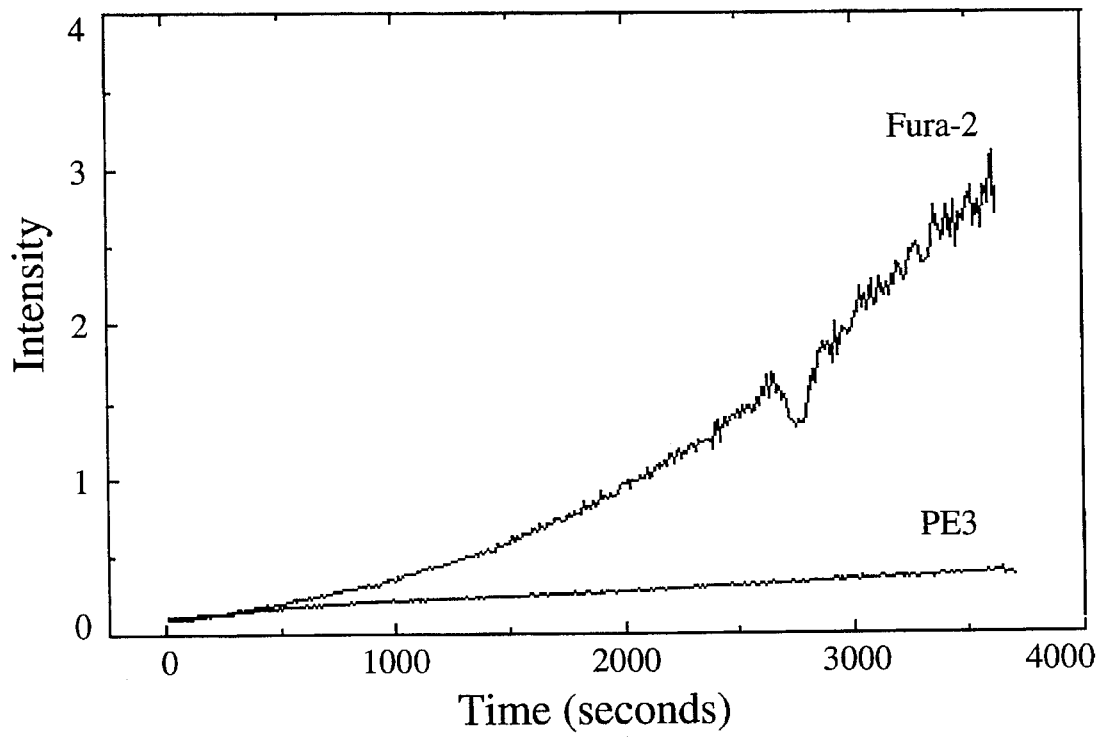
Figure 8

Response of PE3 to changes in intracellular calcium stimulated by the lectin Concanavalin A calcium ionophore ionomycin, and permeabilization of the plasma membrane followed by th addition of the calcium chelator EGTA.

Diagram of smooth muscle cell showing position of scanline

Intensity Profile of Scanline Before and After Injection of FFP18.

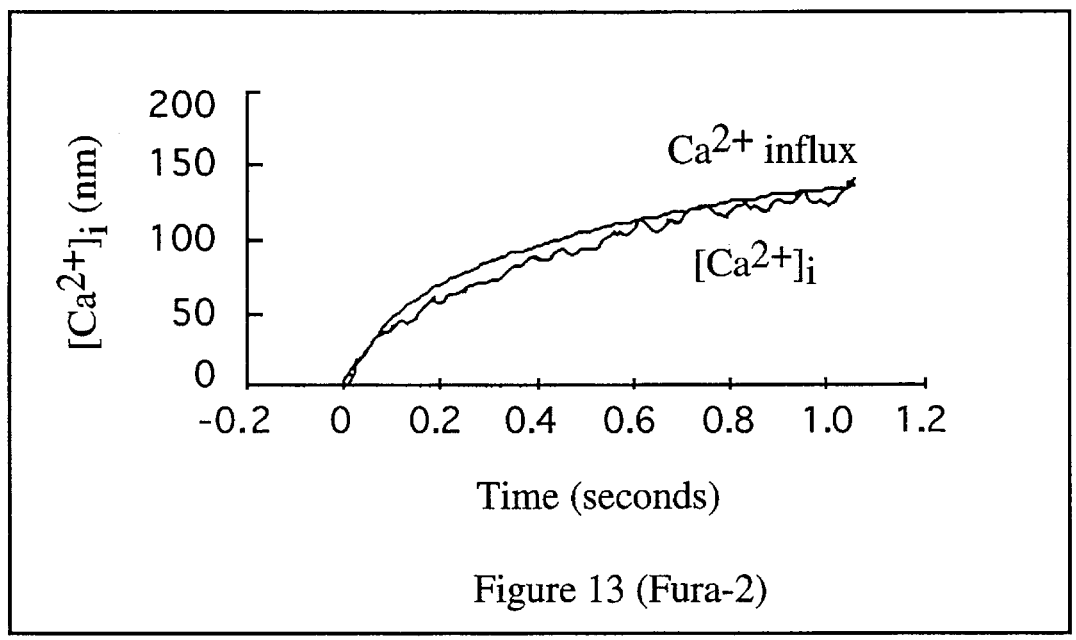
Figure 13 (Fura-2)
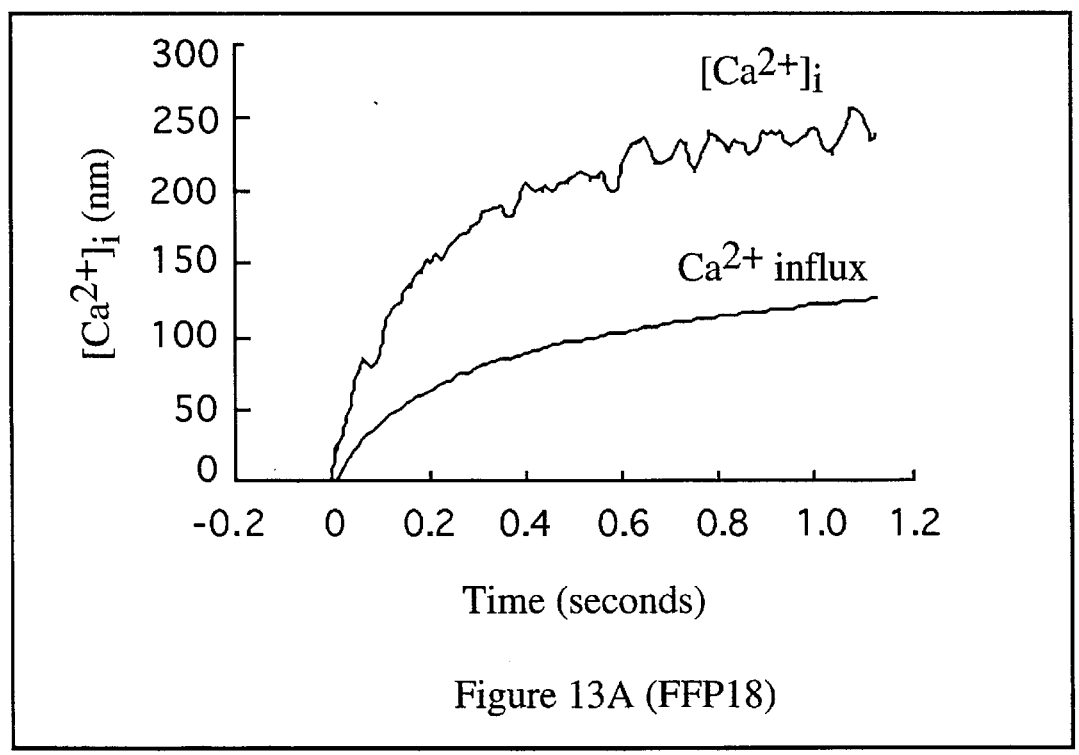
Figure 13A (FFP18)

FLUORESCENT CALCIUM INDICATORS TARGETED TO SPECIFIC INTRACELLULAR ENVIRONMENTS

STATEMENT AS TO ANY INVENTION RIGHTS UNDER FEDERALLY SPONSORED RESEARCH

This invention was made with government support under grant GM40605 from the NIH and Grants DCB 8858186 and DIR 9022325 from the National Science Foundation. The government has certain rights in this invention.

BACKGROUND OF THE INVENTION

1. Field of the Invention

The present invention relates to new tetracarboxylate fluorescent calcium indicators which are targeted to specific intracellular environments, locations or compartments. These new indicators include (1) PE3, a zwitterionic indicator which resists leakage and compartmentalization and therefore remains cytosolic and (2) FFP18, an amphipathic indicator which binds to cellular membranes and therefore reports calcium in the vicinity of the membrane. Each of these indicators are derived from a new BAPTA-based chelator moiety which serves as a convenient and flexible starting point for generating a wide variety of new calcium indicators while retaining the ion selectivity and pH insensitivity of BAPTA.

2. Background of the Invention

Many external environmental signals produce changes in cellular activities or behavior by causing a change in the intracellular free calcium concentration. Thus a proper understanding of cell physiology is often critically dependent on the ability to monitor changes in cellular calcium concentrations. The introduction of fura-2 and indo-1 provided revolutionary new approaches for studying calcium in individual cells. These indicators were much brighter than their predecessor, quin2, and made it possible to measure calcium based on the ratio of fluorescence intensity at two excitation or emission wavelengths. The feasibility of ratio-based measurements quickly stimulated the development of fluorescence ratio fluorometric instruments and imaging systems and has led to a multitude of new findings regarding the spatial and temporal apsects of calcium regulation in cells.

The rapid adoption of fura-2 and its relatives, and the experience gained in using these indicators also quickly revealed several problems related to dye loading, such as leakage or compartmentalization, spectral alterations between intracellular dye and that in in free solution and unwanted binding to cellular constituents. Furthermore, it has become apparent that fura-2 does not always faithfully report rapid changes in calcium seen in some excitable cells and may altogether miss some rapid and/or highly localized calcium transients.

The problem of fura-2 leakage and compartmentalization was first noted in the consistent failure of fura-2/AM to load in PTK1 cells. Efforts to improve loading using Pluronic f127 gave cells that were initially bright but with time, the indicator rapidly leaked out of the cell leaving only perinuclear vesicles that were still brightly fluorescent. Loss of cytosolic indicator was retarded when cells were incubated at lower temperatures, suggesting that some cellular transport system was involved. Additional information was obtained from experiments in which a variety of different tetracarboxylate indicators were iontophoresed into the cytosol of Tradescantia cells (Hepler and Poenie, unpublished). The initial cytosolic fura-2 distribution was obvious because the indicator spread rapidly to adjacent cells. However, within a short time, virtually all of the cytosolic indicator was transferred to the vacuole. This result showed that cells had mechanisms for actively transporting the anionic form of the indicator. The one indicator which differed in this respect was rhod-2, which, unlike the other indicators, contained a positive charge. This suggested that a zwitterionic indicator might be less susceptible to leakage and compartmentalization. Reports that anion transport inhibitors suppressed the leakage and compartmentalization of fura-2 added further support for this hypothesis.

Although keeping cells at lower temperatures or using anion transport inhibitors such as probenecid and sulfinpyrazone can help reduce leakage and compartmentalization, they add additional variables to the experiment. Conjugation of indicators to dextrans provides another method for preventing dye leakage and compartmentalization but these indicators must loaded into cells by microinjection. The use of rhod-2 would seem to be a good solution to the problem but unfortunately, rhod-2 exhibits neither the spectral shift seen with fura-2 nor the large increase in fluorescence exhibited by fluo-3. As a result, it has not been nearly as popular as the other indicators.

Another problem, which has been the subject of considerable dispute, is how faithfully fura-2 tracks cellular calcium transients. Work by Hollingsworth and Baylor suggested that fura-2 was not fast enough to follow rapid changes in muscle calcium and was unable to track calcium levels at their peak. More enigmatic were cases such as the report of Kao, et. al., where a variety of indirect measures indicated the existence of a calcium transient during mitosis but these were seldom seen when monitored with fura-2. While the absence of a calcium transient might be the right result, it also seemed possible that calcium transients were sufficiently fast and/or localized to preclude detection with fura-2. This latter possibility has gained credence with a recent report showing that large but highly localized increases in calcium do occur in cells and these transients are not readily detected using fura-2. To circumvent this problem it was necessary to develop indicators which responded more quickly to changes in calcium and placed them nearer to the source of the calcium increase.

OBJECTS OF THE INVENTION

It is an object of the present invention to provide a new class of fluorescent calcium-specific indicators that are useful for measuring calcium in specific intra cellular environments.

It is a further object of the present invention to provide indicators which can resist leakage out of cells by virtue of the presence of one or more positive charges.

It is a further object of the present invention to provide a modified BAPTA backbone structure of fura-2 to give a zwitterionic indicator by virtue of the presence of one or more free amino groups which can ionize at physiological intracellular pH values to give an indicator containing 1 or more positive charges.

It is a further object of the present invention to provide zwitterionic calcium indicators where the unprotonated and protonated forms of the free amine group are insulated from the aromatic BAPTA rings so that either form of the amine has little impact on the calcium dissociation constant.

It is a further object of the present invention to introduce one or more free amino groups in such a form that they are resistant to quaternization.

It is a further object of the present invention to produce zwitterionic calcium indicators which can be converted to acetoxymethyl esters so that cells can be loaded with the indicator using conventional acetoxymethyl ester loading techniques.

It is a further object of the present invention to provide indicators which adhere or insert into cell membranes and report calcium levels near the membrane.

It is a further object of the present invention to provide intracellular calcium indicators which are prevented from penetrating too deeply into the membrane because of a charged bridge which separates the hydrophobic tail from chelator portion of the indicator.

SUMMARY OF THE DRAWINGS

FIG. 7 and 7A is a set of graphs comparing the rates of dye leakage for cells loaded by the acetoxymethyl ester technique, using either fura-2/AM or PE3/AM, Example 4.

FIG. 8 is a graph showing how apparent baseline calcium values drift due to leakage of either fura-2 or PE3 out of the cell.

FIG. 13 and FIG. 13A are graphs showing comparisons of the amount of $Ca^{2+}$ after periods of time for both fura-2 and FFP 18, Example 7.

DEFINITION OF TERMS USED HEREIN

Figure 1:
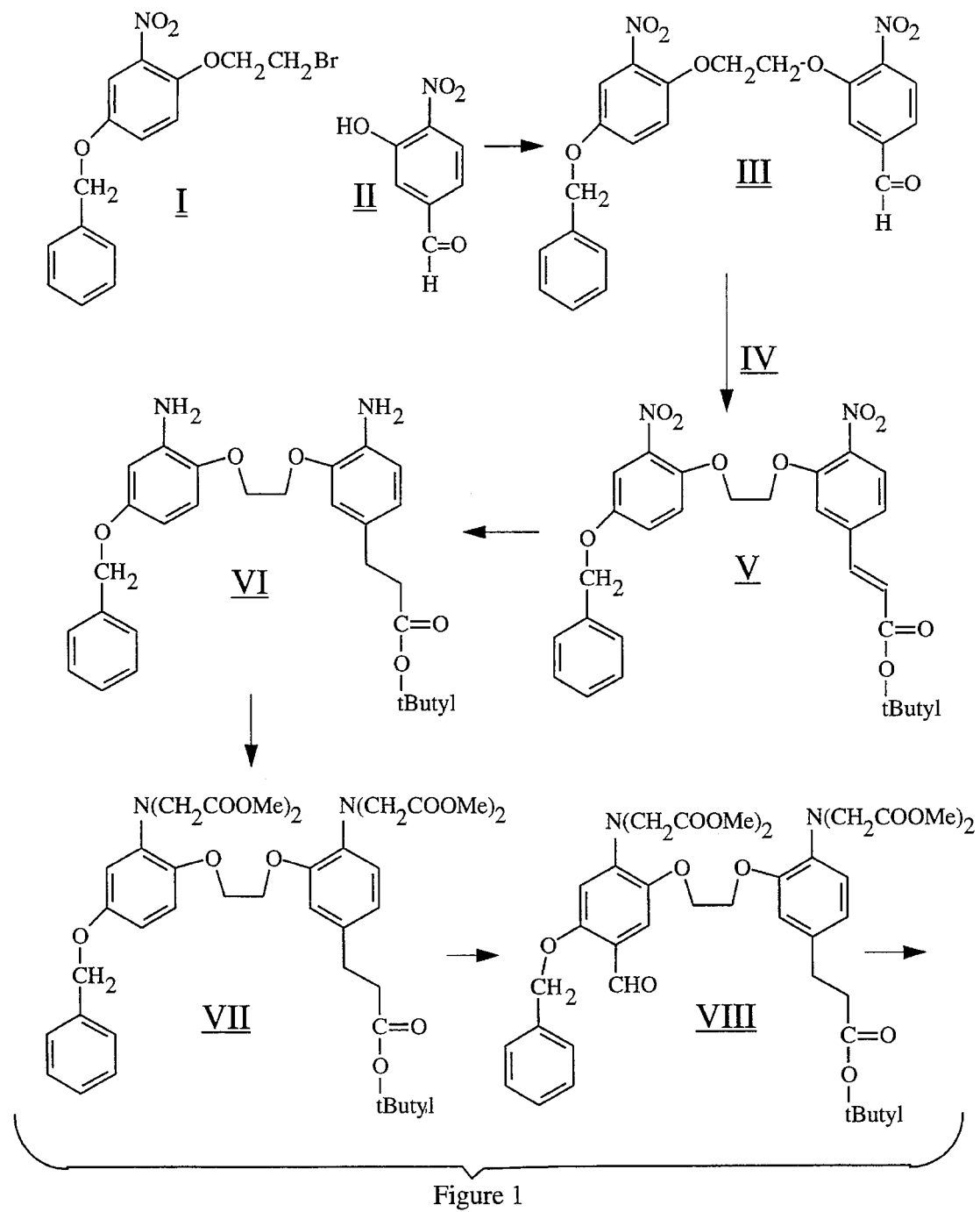
FIG. 1 is Page 1 of 2 of a chemical flow chart illustrating the first pad of a synthetic pathway leading to PE3 and FFP18, via I through VII.

As used herein $[Ca^{2+}]i$ means intracellular free calcium concentration

As used herein BAPTA means 1,2 bis(2-aminophenoxy) ethane N,N,N'N'-tetraacetic acid.

As used herein EGTA means ethylene glycol bis(beta-aminoethyl ether)N,N,N'N'tetraacetic acid.

As used herein, BAPTA-like means substituted derivatives of BAPTA which retain the essential characteristic of two bis(carboxymethyl)amino-substituted phenyl rings, said rings being linked at the positions ortho to the amines through a four atom bridge wherein the atom adjacent to each phenyl ring is 0 and the two center atoms are each C.

As used herein fura-2 like means substituted derivatives of fura-2 where substitutions are designed to add new functionality to the indicator.

As used herein fura-2 means 1-(2-(5-ethoxycarbonyloxazol-2-yl)-6-aminobenzofuran-5-oxy)-2-(2'-amino-5'-methylphenoxy)ethane-N,N,N'N'-tetraacetic acid.

As used herein, MOPS means 3-(N-morpholino)propane-sulfonic acid. The new dyes disclosed herein are named as fura-derivatives.

As used herein, mM means $10^{-6}$ moles/liter and nM means $10^{-9}$ moles/liter.

As used herein HBSS means Hanks Balanced Salts Solution, a physiological medium for maintaining cells in a healthy condition.

REFERENCE LIST

F. DIVIRGLIO ET AL., *Inhibition of fura-2 Sequestration and Secretion with Organic Anion Transport Blockers*, 11 CELL CALCIUM 57 (1990).

G. GRYNKIEWICZ ET AL., *A New Generation of Fluorescence Indicators with Greatly Improved Fluorecence Properties*, 260 J. BIOL. C., 3440 (1985).

P. HEPLER AND D. CALLAHAN, *Free Calcium Increases During Anaphase in Stamen Hair Cells of Tradescantia*, 105 J. CELL. BIOL. 2137 (1987).

S. HOLLINGWORTH AND S. BAYLOR, *fura-2 Signals from Intact Frog Skeletal Muscle Fibers*. 15 BIOPHYS. J. 549a (1987).

J. KAO ET AL., *Active Involvement of Calcium in Mitotic Progression of Swiss 3T3 Fibroblasts*, 111 J. CELL. BIOL. 183 (1990).

MARTIN POENIE, *Measurement of Intracellular Calcium with Fluorescent Calcium Indicators*. INTRACELLULAR MESSENGERS 20 (1992).

E. R. RICHIE ET AL., *Murine T-lymphomas Corresponding to the Immature CD4–CD8+ Thympcyte Subsets*, 1 DEV. IMMUNOLOGY 255 (1991).

R. TSIEN, *New Calcium Indicators and Buffers with High Selectivity Against Magnesium and Protons: Design, Synthesis, and Properties of Prototype Structures*, 19 BIOCHEMISTRY 2396 (1980).

R. TSIEN, *A Non-disruptive Technique for Loading Calcium Buffers and Indicators into Cells*, 290 NATURE 527 (1981).

R. TSIEN ET AL., *Measurement of Cytosolic Free $Ca^{+2}$ in Individual Small Cells Using Fluorescence Micrescopy with Dual Excitation Wavements*, 6 CELL CALCIUM 145 (1985).

DESCRIPTION OF THE INVENTION

Brief Description of the Invention

The present invention is a new family of calcium indicators which can be readily modified and targeted to-different regions of the cell. These new indicators are derived from a modified BAPTA backbone which contains a flexible attachment point for adding new functionality to the indicator without greatly affecting chelation or the fluorescence characteristics of the chromophore. One derivative gives PE3, a zwitterionic fura-2 analog which resists leakage and compartmentalization. A second derivative, FFP18, contains a 12 carbon hydrophobic tail which targets this indicator to cell membranes. FFP18 is a near membrane indicator and it reports much faster and larger calcium transients than fura-2 as well as localized changes in cellular $Ca^{2+}$.

Detailed Descriptions of the Drawings

Figure 2:
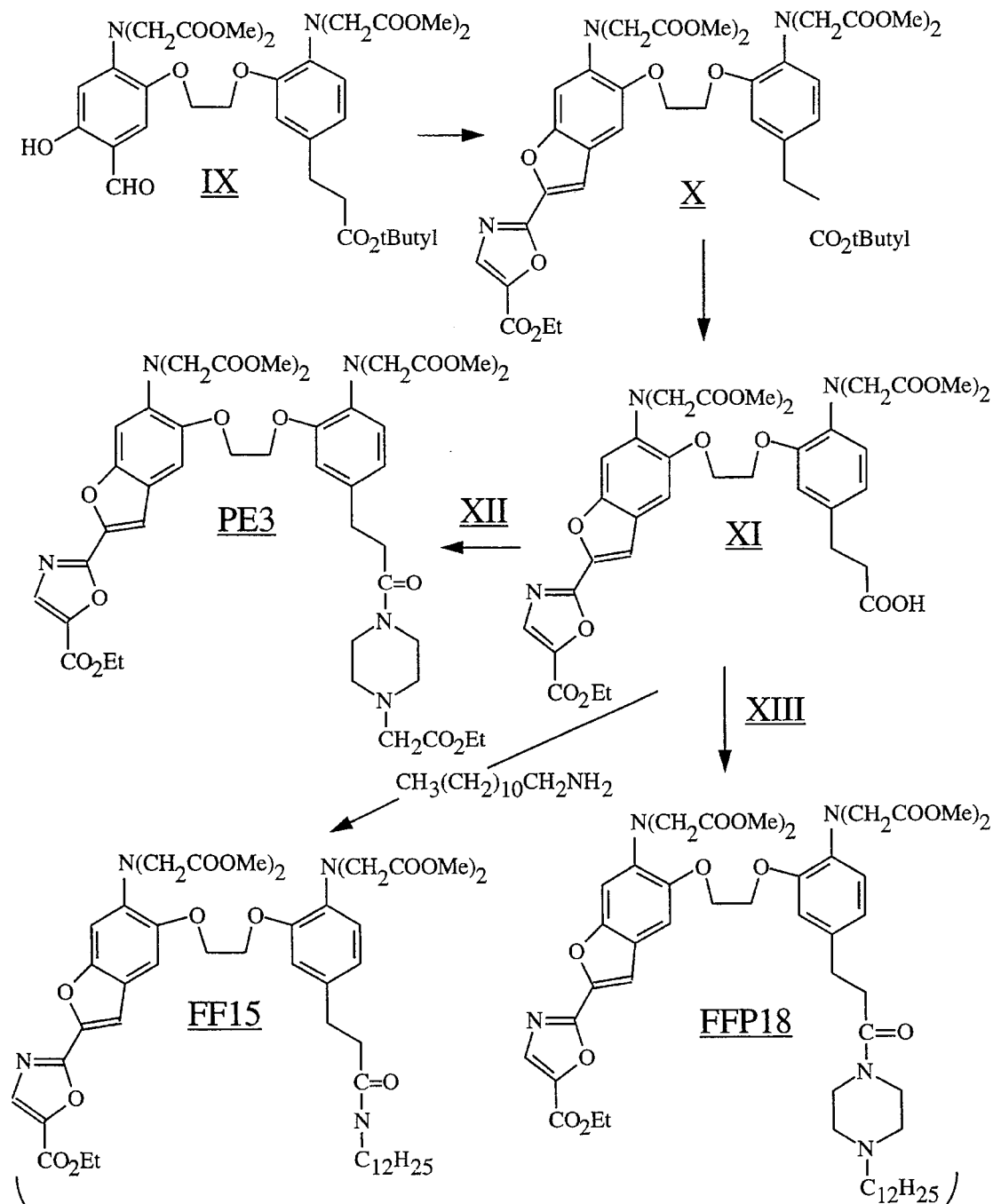
FIG. 2 is Page 2 of 2 of the chemical flow chart illustrating the remainder of the synthetic pathway leading to PE3 and FFP18, via VIII through XIII.

FIGS. 1 and 2 shows the synthetic pathway leading to PE3, FF15 and FFP18. The Roman numerals used in the figure are keyed to the synthetic details discussed in the METHODS OF SYNTHESIS section, infra.

Figure 3:
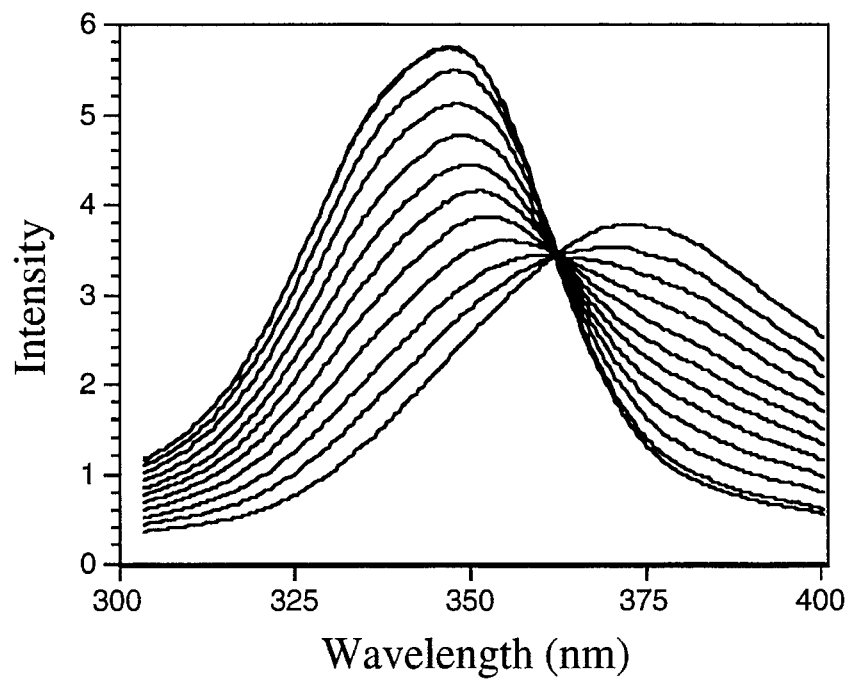
FIG. 3 is a graph showing a family of excitation spectra for FFP18 at 20° C. in buffers with free $Ca^{2+}$ values ranging from <1 nM to >10 mM.

FIG. 3 shows the results of titration of FFP18 with calcium. A series of excitation spectra were obtained from a solution containing 130 mM KCl, 20 mM NaCl, 10 mM KMOPS, 1 mM $Mg^{2+}$, 10 mM CaEGTA (EGTA) and 333 nM FFP18 as free calcium concentration was incrementally adjusted. Calcium concentration was varied by adjusting ratio of CaEGTA/EGTA, so that free calcium varied from less than 1 nM to 1 mM. During the titration, temperature was held constant at 37° C. by a circulating water bath and $Mg^{++}$ levels were held at a fixed concentration of 1 mM. The excitation spectra were recorded between 300 and 400 nm by a Photon Technology Intl. Alpha Scan fluorometer where the excitation band width was set 6 nm and the emission was collected at 485 nm with 4 nm band width. The titration was done starting with 3 ml of 130 mM KCl, 20 mM NaCl, 10 mM K-MOPS, 1.07 mM EGTA, 1.07 mM $MgC_{12}$, 333 nM FFP18 and adjusting the pH to 7.2 and recording the spectrum. 1M $K_2CaEGTA$ was added directly to the solution to incrementally increase free calcium.

Figure 4:
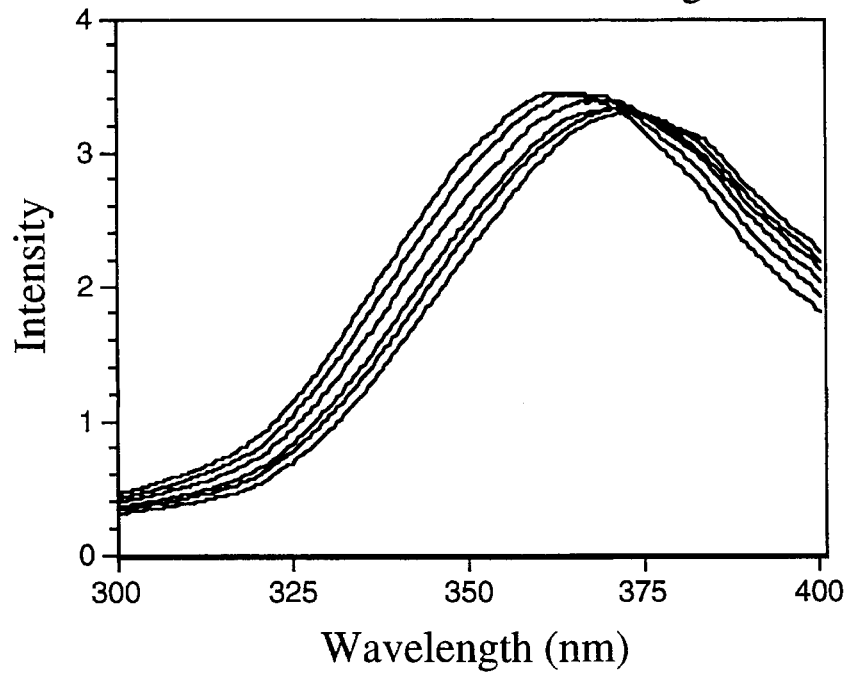
FIG. 4 is a graph showing the effect of $Mg^{2+}$ on FFP18.

FIG. 4 shows the effect of $Mg^{2+}$ on FFP18. The excitation spectrum was recorded of 1 μM FFP18 in 2.5 ml of 130 mM KCl, 20 mM NaCl, 1 mM EGTA, 10 mM MOPS, pH 7.05 at 37° C. Then 25 μl of the solution was replaced with 25 μl of a solution containing 1 μM of that same dye, 111.2 mM $MgC_{12}$, 12.2 mM EGTA, 10 mM MOPS, pH 7.05. This exchange yielded 1 mM free $Mg^{2+}$ 0.2 and 5 mM free $Mg^{2+}$ were obtained by successively exchanging 25.25 and 76.53 μl of the original solution with that of the latter solution containing the high concentration of $Mg^{2+}$. Emission was collected at 490 nm for fura-PE3 and 485 nm for FFP18, 4 nm band pass, and excitation 5 nm band pass.

Figure 5:
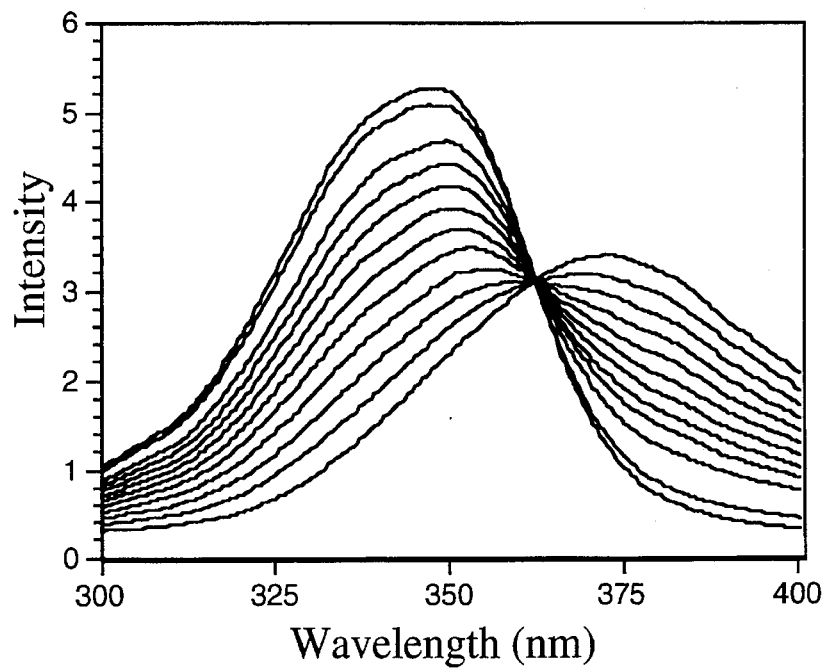
FIG. 5 is a graph showing a family of excitation spectra for PE3 at 20° C. in buffers with free $Ca^{2+}$ values ranging from <1 nM to >10 mM.

FIG. 5 shows the results of titration of PE3 with calcium. A series of excitation spectra were obtained from a solution containing 130 mM KCl, 20 mM NaCl, 10 mM KMOPS, 1 mM $Mg^{2+}$, 10 mM CaEGTA (EGTA) and 1 mM PE3 as free calcium concentration was incrementally adjusted. Calcium concentration was varied by adjusting ratio of CaEGTA/EGTA so that free calcium varied from less than 1 nM to 1 mM. During the titration, temperature was held constant at 37° C. by a circulating water bath and Mg++ levels were held at a fixed concentration of 1 mM. The excitation spectra were recorded between 300 and 400 nm by a Photon Technology Intl. Alpha Scan fluorometer where the excitation band width was set 6 nm and the emission was collected at 485 nm with 4 nm band width. The titration was done starting with 3 ml of 130 mM KCl, 20 mM NaCl, 10 mM K-MOPS, 1.07 mM EGTA, 1.07 mM $MgC_{12}$, and 1 mM PE3 adjusting the pH to 7.2 and recording the spectrum. 1M $K_2CaEGTA$ was added directly to the solution to incrementally increase free calcium.

Figure 6:
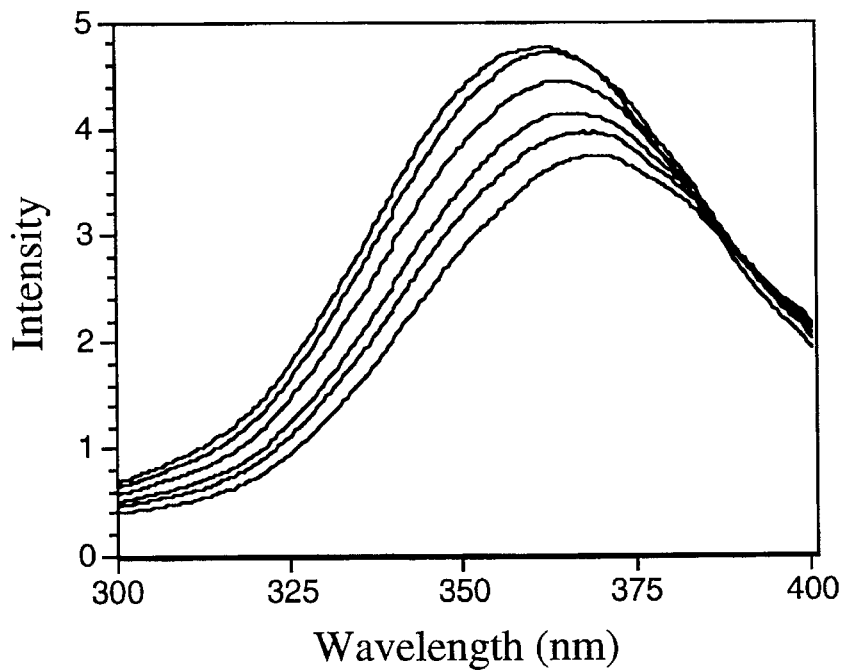
FIG. 6 is a graph showing the effect of $Mg^{2+}$ on PE3.

FIG. 6 shows the effect of $Mg^{2+}$ on PE3. The excitation spectrum was recorded of 1 μM PE3 in 2.5 ml of 130 mM KCl, 20 mM NaCl, 1 mM EGTA, 10 mM MOPS, pH 7.05 at 37° C. Then 25 μl of the solution was replaced with 25 μl of a solution containing 1 μM PE3, 111.2 mM $MgC_{12}$, 12.2 mM EGTA, 10 mM MOPS, pH 7.05. This exchange yielded 1 mM free $Mg^{2+}$. The 2 and 5 mM free $Mg^{2+}$ concentrations were obtained by successively exchanging 25.25 and 76.53 μl of the original solution with that of the latter solution containing the high concentration of $Mg^{2+}$. Emission was collected at 490 nm for fura-PE3 and 485 nm for FFP18, 4 nm band pass, and excitation 5 nm band pass.

FIG. 7 and FIG. 7A show the leakage of indicator from 322 T lymphoma cells loaded with fura-2 or PE3. The T cell lymphoma cell line was loaded with 1 mM fura-2/AM or 1 mM PE3/AM for 30 minutes. Afterwards, an aliquot of dye loaded cells were placed in a cuvette and the fluorescence at 360 nm was recorded. Then, 5 mM $Ni^{2+}$ was added to quench any indicator that was outside the cells. The remainder of the loaded cell suspension was incubated for 1 hour at 37° C. Then a second aliquot was removed placed in a cuvette together with 5 mM $Ni^{2+}$ and fluorescence recorded. The difference in fluorescence of $Ni^{2+}$ treated cells between the 0 hour time point and the one hour time point represents indicator that leaked out of the cells into the extracellular medium over the 1 hour incubation period.

FIG. 8 show the impact of dye leakage on apparent baseline or resting levels of cellular calcium. A quantity of 322 T-lymphoma cells were loaded with either 1 mM fura-2/AM or 1 mM PE3/AM for 1 hour, washed and resuspended in HBSS containing 1% fetal bovine serum. An aliquot of the loaded cell suspension was then placed in the cuvette of an Alpha Scan fluorometer and the fluorescence signal was recorded over time, as the cells were alternately excited at 340 nm and 380 nm. Calcium concentration was calculated from the 350/385 nm fluorescence ratio as described by Tsien, et al.(1985). The results show a continuous increase in apparent intracellular calcium levels of the fura-2 loaded cells. This is due to the leakage of indicator from the cytoplasm of the cell where calcium levels are very low ($10^{-7}M$) into the extracellular medium which contains 1 mM calcium. With PE3, the small change in baseline intracellular calcium levels reflects the lower leakage rate out of the cell.

Figure 9:
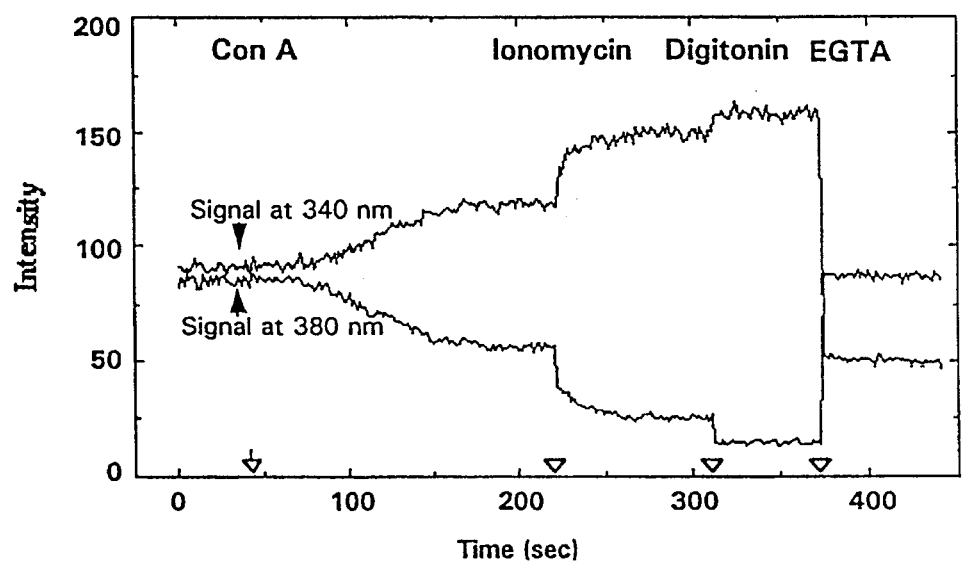
FIG. 9 is a graph showing the response of PE3 to changes in intracellular calcium stimulated by the addition of an activating cell surface ligand, ConA or calcium specific ionophores, Example 3.

FIG. 9 shows the responsiveness of PE3 loaded cells to changes in intracellular calcium. A quantity of 322 T-lymphoma cells were loaded with 1 mM PE3 for 1 hour, washed and resuspended in HBSS containing 1% fetal bovine serum. An aliquot of this loaded cell suspension was then placed in a cuvette and the fluorescence was measured while alternating between 350 nm and 380 nm excitation. Baseline measurements were recorded for about 50 sec and then cells were stimulated with 50 mg/ml Concanavalin A (first arrow) which activates T cells by ligating the T cell antigen receptor. After cells had responded to Concanavalin A, calcium ionophore was added (second arrow) to elevate calcium further. Cells were then lysed with digitonin, a detergent which selectively lyses the plasma membrane of cells and releases the cytosolic indicator into the medium where calcium levels are high (1 mM). This gives the maximum ratio of fluorescence at 340 nm/380 nm. Subsequently, EGTA was added to reduce free calcium levels to 10–9M. When calcium levels are reduced, fluorescence at 380 now becomes much brighter while the fluorescence at 340 becomes dim.

Figure 10:
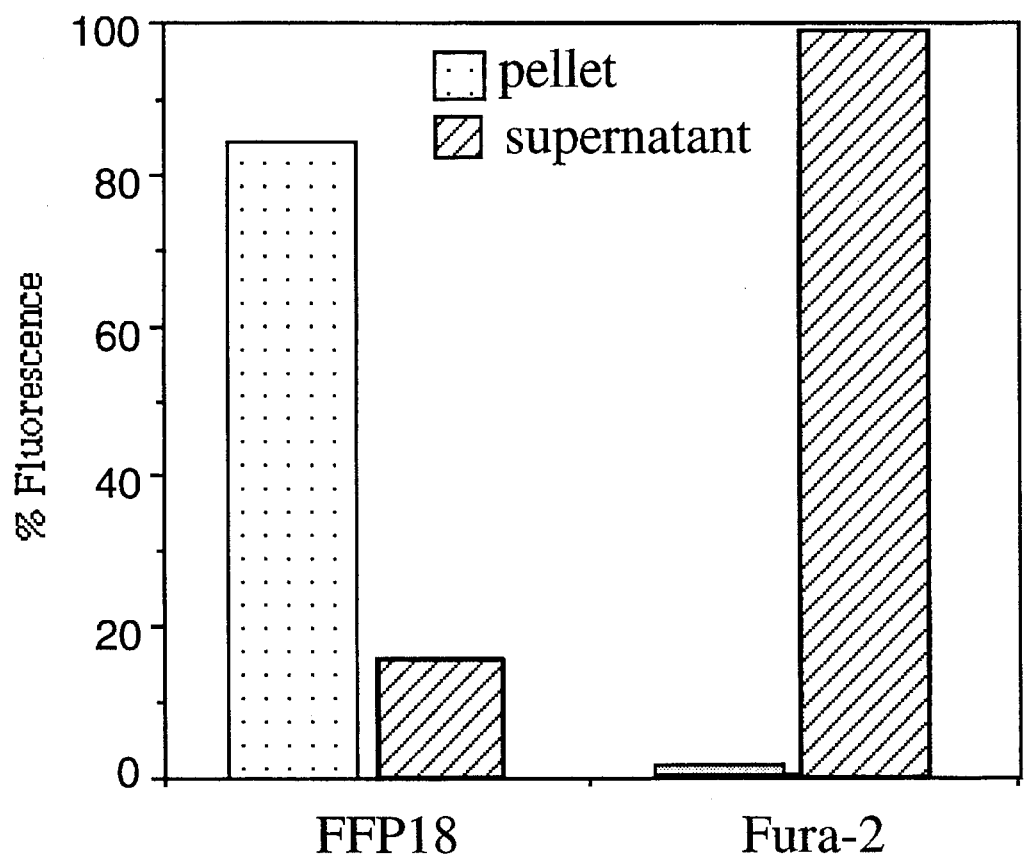
FIG. 10 is a graph comparing the avidity of FFP18 and fura-2 for synthetic lipid membranes.

FIG. 10 shows the avidity of FFP18 and fura-2 for artificial lipid bilayers. Negatively charged liposomes were prepared from a kit (SIGMA) by the hand-shaking method, resuspended in 100 mM KCl, 10 mM HEPES, pH 7.2 (buffer A). To achieve binding to liposomes, 2 μmole fura-2 or FFP18 were incubated with 3.6 μmoles of liposomes for 4 hours at room temperature. The loaded liposomes were centrifuged overnight at 70,000×g. The pellet was washed once with buffer A and centrifuged at 70,000× g for 4 hours. The resulting supernatants and pellets were each brought to 3 mls final volume in buffer A. Fluorescence intensities at 362 nm excitation, 510 nm emission were recorded on a PTI alphascan fluorometer. Slit widths were 1 mm for excitation slits, and 1 nm and 0.5 mm for emission slits. Bandpass was 4 nm/mm. The fluorescence intensity of the wash from fura-2 loaded liposomes was used as an indicator of fluorescence as a result of dye trapped by liposomes during centrifugation.

Figure 11:
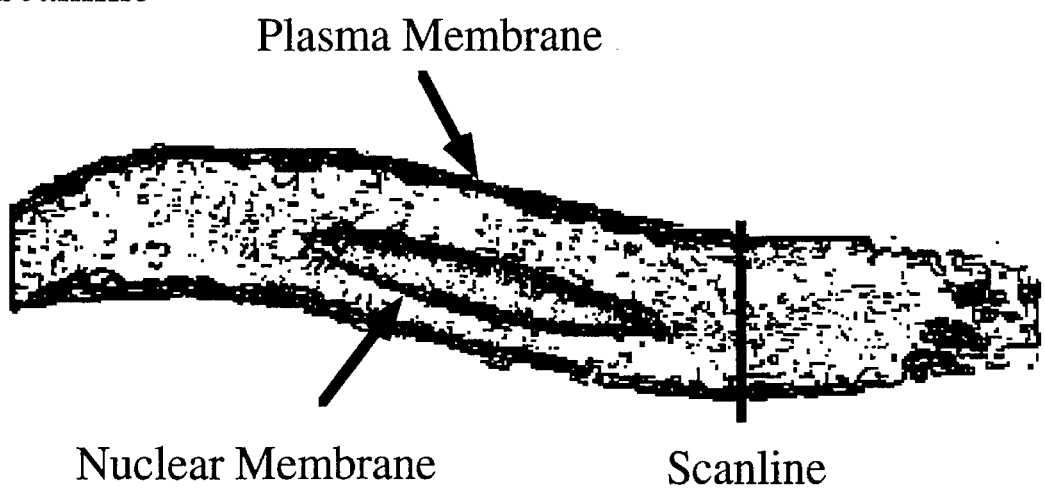
FIG. 11 is a graph of a cell showing the Calcium at the membranes and in FIG. 11A the scanline intensity profile before and after injection of the cell with FFP 18, Example 5 is shown.
Figure 11A:
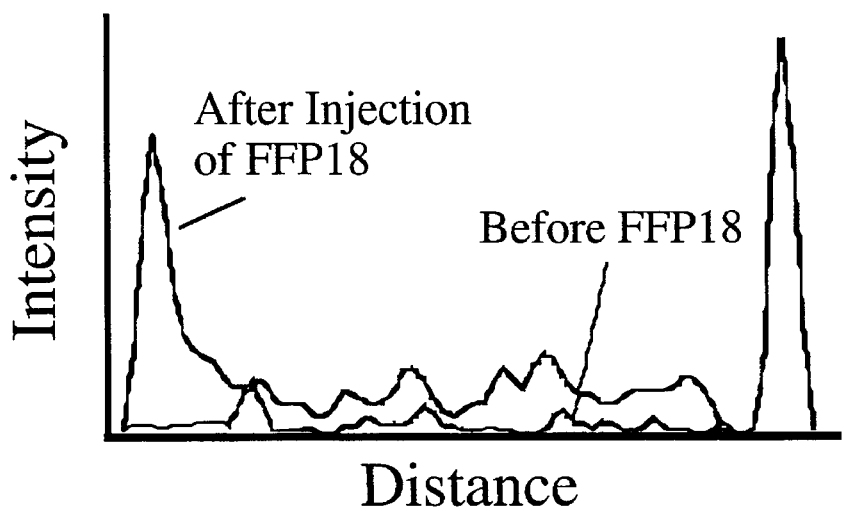

FIG. 11 and FIG. 11A show the intracellular distribution of FFP18. In Example 5, the potassium salt of FFP18 was microinjected into individual smooth muscle cells. A fluorescence image of a smooth muscle cell was recorded before and after microinjection of FFP18. The location of calcium is shown in FIG. 11 while a single scan line is shown for a cross section of the muscle in FIG. 11A. As can be seen, the majority of the fluorescence is associated with the plasma membrane and nuclear membrane.

Figure 12:
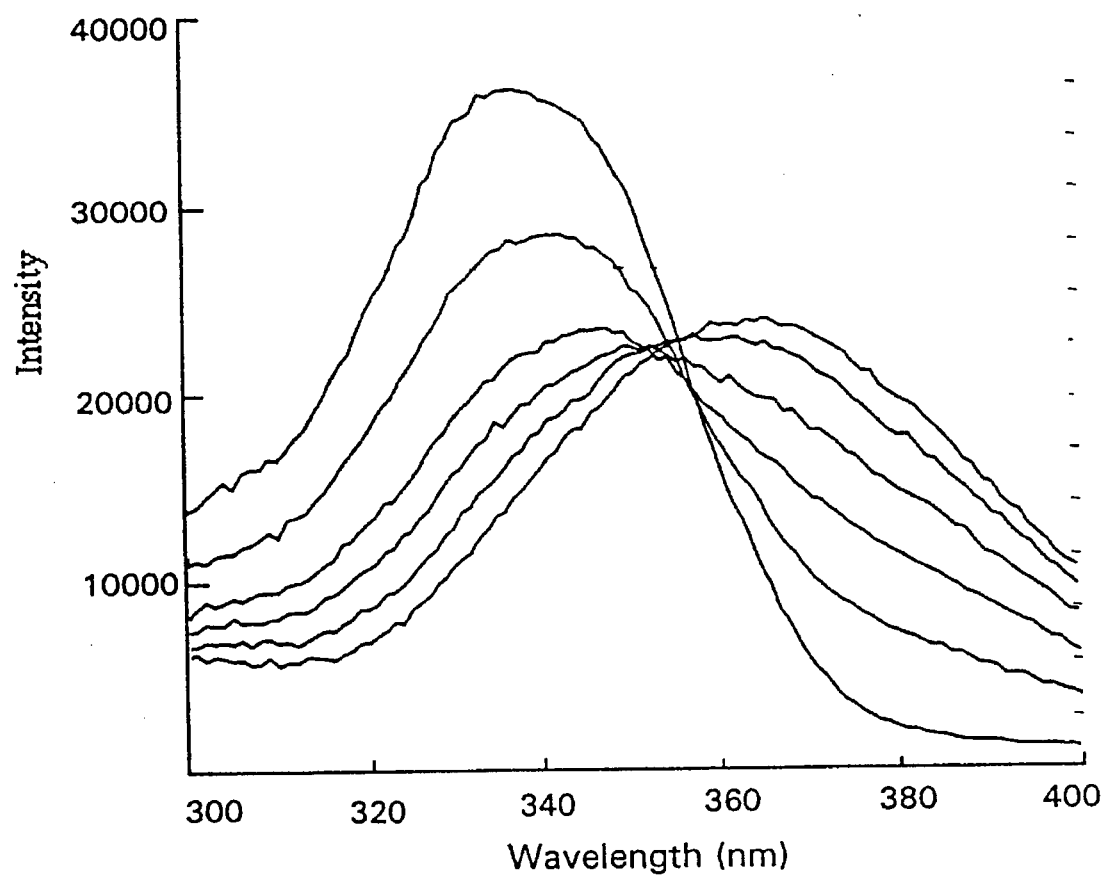
FIG. 12 is a graph showing results of titration of FFP 18 after microinjection into cells, Example 6.

FIG. 12 shows spectra of fluorescence response in calcium obtained from FFP18 microinjected into cells.

FIG. 13 and FIG. 13A show the relationship between the intracellular [$Ca^{2+}$] transients over time for fura-2 and FFP18. In Example 7, the relationship between the intracellular [$Ca^{2+}$] transients reported by FFP18 or fura-2 and calculated [$Ca^{2+}$] transients representing calcium influx are shown as a function of time. The amount of $Ca^{2+}$ entering the cell across the membrane was calculated by integrating the inward current signal and converting the charge to moles of $Ca^{2+}$ per cell volume. This [$Ca^{2+}$] was divided by the average buffering capacity of these cells. FIG. 13 shows the resulting smooth curve representing intracellular [$Ca^{2+}$] due entirely to $Ca^{2+}$ influx across the plasma membrane without $Ca^{2+}$ re-uptake mechanisms in operation. It indicates that the magnitude of the recorded and calculated increases in [$Ca^{2+}$] were similar. The [$Ca^{2+}$] transients reported by the calcium indicators are shown by the more noisy traces. The graph (A)Fura-2 shows an example of the data In contrast, the increases in [$Ca^{2+}$] recorded by FFP18 in 4 different cells was much larger than the calculated calcium transients giving a ratio of 2.6+/−1.0 [nM (recorded/nM (calculated)], as shown in the graph (B)FFP18. These results suggest that [$Ca^{2+}$] rises much higher near the membrane where FFP18 is reporting calcium.

FIG. 14, FIG. 14A, FIG. 14B, and FIG. 14C represent the data obtained from Example 8, a sample of the data obtained from one of the 4 cells where the [$Ca^{2+}$] transient was recorded using fura-2 and FFP18. The ratio of calcium influx measured using fura-2 to the calcium influx calculated from the integral of the current at the 200 msec time point gives a value of 0.9+/−0.05 [nM (recorded)/nM(calculated)].

DESCRIPTION OF THE PREFERRED EMBODIMENT(S)

Brief Description of Preferred Embodiments

The present invention comprises a new class of fluorescent BAPTA-like calcium indicators which are rendered zwitterionic by the introduction of one or more ionizable amine groups. Fura-2 is intended to function with no ionized amino groups. PE3 and FFP18 intentionally incorporate ionized amino groups. These indicators are based on a new BAPTA backbone structure which can be flexibly and easily modified to give calcium indicators with a variety of new properties. Examples are a piperazinoacetic acid which gives indicators which resist leakage out of the cell. In another case, a dodecylpiperazine was genrated which gives a near membrane calcium indicator.

Detailed Description of Preferred Embodiments

The invention disclosed herein is a new family of fluorescent calcium indicators designed as derivatives of the BAPTA-like fluorescence calcium indicators fura-2 and indo-1, where modifications made to the right side BAPTA ring to give new functionality to the indicator while having a minimal impact on the fluorescence or chelation properties of the indicator. Different kinds of new functionality are obtained by varying a series of R groups (R1–R3) attached to the right side BAPTA ring. Examples of the new functionalities include resistance of the new indicators to transport or leakage out of the cell and insertion of the indicator into the cell membrane lipid bilayer so that the indicator functions as a "near membrane" indicator. In these new indicators, R1 is changed from $CH_3$ to $CH_2$—R where R becomes either a benzylic carbon linked to R2 or a carboxymethyl group linked to R2. The second R group (R2) contains an ionizable amine so that the indicator has a positive charge at physiological pH values and which is sufficiently hindered to resist quaternization in the presence of acetoxymethyl bromide. The third R group (R3) consists of either (1) an acetate linked through the alpha carbon to the piperazine amine, or (2) an aliphatic carbon chain varying in length from $C_4$ to $C_{18}$ linked to the piperazine amine.

METHODS OF SYNTHESIS

Methods were developed for synthesizing the new dyes disclosed herein include the following analogs of fura-2 as shown below:

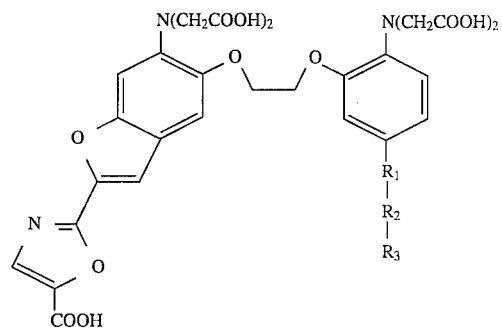

and analogs of Indo-1 as shown below:

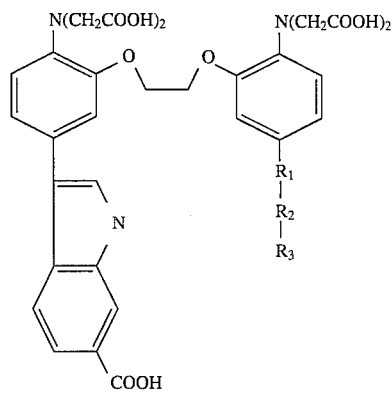

The present invention comprises a new class of fluorescent calcium-specific indicator dyes. Preferred examples of these new dyes are PE3 and FFP18. FIG. 1 and FIG. 2 outline the synthetic route utilized in preparing these Compounds. Full descriptions of the reaction conditions are described below. In both the figures and the discussion that follows, Roman numerals are used to identify the various chemical Compounds. The invented Compounds are designated PE3, FFP18 and FF15.

The synthesis of the Compounds claimed herein is described in the detailed synthesis of PE2, PE3, FF14 and FFP18. Those skilled in the art will recognize new forms of these dyes by using related synthetic methods and starting materials. To that end, we point out that the key intermediate in the synthesis of the invented Compounds III, XI and XII.

The new indicators PE3 and FFP18 are analogs of the fluorescent calcium indicator, fura-2 which is in turn a derivative of BAPTA. In PE2, PE3, FF14 and FFP18 the right hand aromatic ring differs from fura-2 and all other BAPTA-like fluorescent calcium indicators. This alteration in design and synthesis give calcium indicators which differ radically in how these indicators function inside the cell. While the simplest approach to developing a zwitterionic indicator was to make derivatives of the fura-2 oxazole carboxylic acid, such indicators were always much dimmer than fura-2. As a result, we focused on changing the BAPTA ring so as to leave the chromophore intact. In trying to keep hydrophobicity to a minimum by minimizing the total number of carbons, a synthesize linking an amino moiety to methyl group on the BAPTA ring was too sensitive to pH. To provide better insulation between the piperazine amine and the aromatic BAPTA ring, PE3 was synthesized. This was achieved by substituting 3-hydroxy-4-nitrobenzaldehyde-(Compound II) for 2-nitro-5-methylphenol which was the starting material used in the original synthesis of fura-2. A Wittig reaction between the aldehyde of Compound III and Compound IV, the phosphorane of tert-butylbromoacetate gave an unsaturated a,b linkage which was then reduced by catalytic hydrogenation, along with the two aromatic nitro groups, to give Compound V. The advantage of using tert-butylbromoacetate is seen later in the synthesis when it becomes necessary to selectively deprotect this carboxyl group while leaving the remaining carboxylate esters intact. Between Compound V and Compound X (FF6) the synthetic steps are virtually identical to those used for the synthesis of fura-2.

FF6 is a key intermediate containing an aliphatic 3 carbon linker arm terminated in a protected carboxyl group. The tert-butyl ester can be selectively removed with TFA to give Compound XI which frees the carboxyl group for further substitution. The two FF6 derivatives synthesized in this study were PE3 and FFP18. With PE3, the inventors sought to incorporate an ionizable amino group that could survive acetoxymethyl esterification without quaternizing. Several different amine derivatives were explored. It was found that methyl 2-(1-piperazine) acetate (Compound XII) could be easily linked to the indicator through an amide linkage. The remaining tertiary amine was resistant to quaternization during subsequent synthesis of the acetoxymethyl ester. The FFP18 derivative incorporates a different piperazine adduct. Here, 1-dodecylpiperazine a hydrophobic 12 carbon tail added to one of the piperazine amino groups. This gives an amphipathic indicator where one end can anchor in cell membranes.

Compound Synthesis

Proton NMR spectra were recorded on a Varian EM390 instrument at 90 MHz. Peaks are reported below using the following convention: NMR(solvent, operating frequency), chemical shift in ppm from TMS (Tetramethyl silane), multiplicity (s=singlet, d=doublet, dd=doublet of doublets, t=triplet, q=quartet, m=mulitplet, br=broad, spin-spin coupling constant if appropriate, integrated number of protons). In cases where several adjacent peaks are too close for their integrals to be separated, the total integral for the cluster is given.

I to III

The fura-2 intermediate I (1.2 g, 2.75 mmoles) and commercially obtained 4-nitro-3-hydroxybenzaldehyde (Compound II, Aldrich) were dissolved in 9 ml dry DMF containing 4 grams of anhydrous $K_2CO_3$ and heated at 120° C. for two hours. The mixture was then poured into water and the resulting precipitate was filtered, washed with water and dried to give Compound III (1.3 g). This residue was used for subsequent steps without further purification.

IV to V

The phosphorane (IV) was prepared by adding 1.75 g tert-butyl bromoacetate was added to a solution containg 2.0 g triphenyl phosphine in benzene (10 ml), producing Compound IV. The resulting precipitate was collected by filtration and dried under vacuum. Subsequently, a mixture containing 1.4 g of IV, 1.3 g of III and 5 g $K_2CO_3$ in 10 ml dry DMF was heated with stirring at 110° C. for 3 hours. The resulting dark brown solution was then extracted with ethyl acetate, washed with brine, dried and evaporated under vacuum. The resulting gum was purified by silica gel chromatography using ethyl acetate:hexane to give 1.2 g of the semisolid Compound V (80% yield). NMR (CDCl3, 90 MHz) 7.85, d, 1H, J=7Hz; 7.40,m, 5H, aromatic; 7.20, m, 6H; 6.40, d, J=7Hz; 5.0, s, 2H; 4.40,s,4H; 1.50, s, 9H.

VI to VII

Compound V (110 mg, 0.2 moles) was dissolved in methylene chloride (10 ml) and hydrogenated using 30 mg of 5% Pt/C in a Parr Hydrogenator at 50 psi H2 for 5 hours. Afterwards, the catalyst was removed by filtration and the solvent evaporated under vacumn to give a homogeneous yellow solid (VI) which was one spot by TLC. The product was then dissolved in 1 ml acetonitrile and alkylated by the addition of 0.35 ml methylbromoacetate, 0.5 ml ethyl diisopropylamine and 30 mg NaI and refluxing overnight. When the reaction had gone to completion, the mixture was diluted with ethyl acetate and filtered to removed the solids. The filtrate was then washed with water, dried over $MgSO_4$ and evaporated under vacuum. Titration of the gummy residue with methanol gave a solid (130 mg, 83%) Compound VII. NMR (CDCl3, 90 MHz) 7.35, s, 5H; 6.80, m, 4H; 6.55, m, 2H; 5.00, s, 2H; 4.30, s, 4H; 4.20, s, 8H; 3.65, s, 12H; 2.80, t, 2H; 2.55, t, 2H; 1.50, s, 9H.

VIII

Compound VII (150 mg, 0.2 moles) was converted to its corresponding aldehyde adduct using the Vilsmeyer formylation method described previously for fura-2. The reaction yielded 110 mg (70%) of Compound VIII. NMR, (CDCl3, 90 MHz) 10.33, s, 1H; 7.20, s+m, 6H; 6.70, m, 3H; 6.30, s, 1H; 5.10, s, 2H; 4.25, s, 4H; 4.20, s, 4H; 4.15, s, 4H; 3.65, s, 6H; 3.60, s, 6H; 2.80, t, 2H; 2.55, t, 2H; 1.40, s, 9H.

IX

Compound VIII (90 mg, 0.13 mmole) was debenzylated by hydrogenation over 20 mg 10% Pd/C in acetic acid at 50 PSI H2 overnight. This gave a quantitative yield of Compound IX. NMR, (CDCl3, 90 MHz) 11.20, s, 1H; 9.60, s, 1H; 6.90, s, 1H; 6.70, m, 3H; 6.10, s, 1H; 4.10–4.30, m, 12H; 3.60, s, 12H; 2.80, t, 2H; 2.50, t, 2H; 1.45, s, 9H.

X

Compound IX (250 mg, 0.34 mmole), 2-chloromethyloxazole (100 mg), K2CO3 (250 mg) and dry DMF (1 ml) were stirred together at 110° C. for 1.5 hours. When TLC showed that the reaction had gone to completion, the mixture was diluted with ethyl acetate, washed three times with water, dried over anhydrous $Na_2SO_4$ and evaporated to dryness under vacuum. The resulting gummy residue solidified upon storage at 0° C.–4° C. overnight and crystallized upon tituration with methanol to give 200 mg of product (67%). NMR (CDCl3, 90 MHz) 7.90, s, 1H; 7.50, s, 1H; 7.10, m, 2H; 6.80, m, 3H; ??? 6.45, q, 2H; 4.40, s, 4H; 4.30, s, 4H; 4.20, s, 4H; 3.65, s, 6H; 3.60, s, 6H; 2.80, t, 2H; 2.60, t, 2H; 1.50, s+t; 12H.

XI

Compound X (40 mg) was dissolved and stirred overnight in a solution containing 20% trifluoroacetic acid in methylene chloride. The solvent was evaporated under high vacuum at room temperature to give a gummy residue (Compound XI) which was reconstituted in freshly distilled methylene chloride and used in subsequent steps without further purification.

XII

Piperazine (5 g, 58 mmole) was dissolved in 30 ml chloroform and 2.2 g (14 mmole) of methyl bromoacetate in 10 ml chloroform was added dropwise with stirring over the course of one hour. The resulting mixture was filtered to removed solids and evaporated to dryness under vacuum. The residue was then reconstituted in chloroform and purified by silica gel chromatography using 10% methanol:chloroform to give 1.5 g of reagent (65%). NMR, (CDCl3, 90 MHz), 3.80, s, 3H; 3.30, s, 2H; 3.05, t,4H; 2.60, t, 4H; 2.00, s, 1H.

XIII

Piperazine (10 gm, 116 mmoles) was dissolved in 50 ml chloroform and dodecylbromide (5 gm, 20 mmole) dissolved in 10 ml chloroform was added dropwise with stirring over the course of 1 hour. The resulting mixture was filtered to remove solids and the filtrate evaporated to dryness under vacuum. The residue was reconstituted in chloroform and purified by silica gel chromatography using 10% methanol:chloroform to give 2 gm of Compound XIII. NMR (CDCl3, 90 MHz) 1.30–1.75,m,25H; 2.30,s,1H; 2.40, t,4H; 2.90,t,4H.

FF15

Compound XI (100 mg), was dissolved in 3 ml freshly distilled methylene chloride and 120 mL of oxalyl chloride was added. The mixture was then stirred for 20 minutes at 55° C. Afterwards the product was dried under vacuum and immediately resuspended in 2 ml of dry methylene chloride. To this solution, 1 ml of methylene chloride containing 200 mg of bromododecane added and the mixture was stirred for 3 hours at room temperature. The resulting crude product was dried under vacuum, resuspended in chloroform and by silica gel chromatography using 10% methanol:chloroform to give 40 mg of FF15 as a gum. NMR(CDCl3, 90 MHz) 7.90,s,1H; 7.50,s,1H; 7.15,d,2H; 6.80,m,2H; 4.20–4.50,m, 12H; 3.70,s,4H; 3.65,s,4H; 1.20–1.50,m,25H.

Fura-PE3

Compound XI (40 mg) was dissolved in 1.0 ml freshly distilled methylene chloride and then 45 mL was added. The mixture stirred for 20 minutes at 55° C. After completion, the product was dried under vacuum and redissolved in 1 ml freshly distilled methylene chloride. To this mixture was added 0.5 ml methylene chloride containing 100 mg of XII. The resulting mixture was stirred for two hours at room temperature to give the crude product Compound XII. This was purified by column chromatography over silica gel eluting with 2% methanol:chloroform to give 25 mg of pure product PE3. NMR, (CD3, 90 MHz) 7.80, s, 1H; 7.40, s, 1H; 7.15, s, 1H; 7.00, d, 2H; 6.70, m, 2H; 4.50, q, 2H; 4.40, s, 4H; 4.30, S, 4H; 4.10, s, 4H; 3.70, s, 3H; 3.60, s, 6H; 3.55, s, 6H; 3.20, s, 2H; 2.80, m, 2H; 2.50, m, 10H.

FFP18

Compound XI (50 mg) was dissolved in 1 ml freshly distilled methylene chloride and to this was added 50 mL of oxalyl chloride. The mixture was then stirred for 20 minutes at 55° C. After completion, the product was dried under vacumn and redissolved in 1 ml freshly distilled methylene chloride. To this mixture was added 1 ml fresh methylene chloride containing 120 mg compound XIII. The resulting mixture was stirred for 3 hours at room temperature and then dried under vacuum. The crude product was redissolved in chloroform and purified by silica gel chromatography using 5% methanol chloroform to give 35 mg of pure product FFP18 as a gum. NMR (CDCL3, 90MHz) 7.80,s,1H; 7.50, s,1H; 7.10,d,2H; 6.85,m,2H; 3.90–4.40,m,16H; 3.50,m,2H; 2.30,m,2H; 1.10–1.5,m,25H.

PE3 acetoxymethyl ester (PE3/AM)

Synthesis of the PE3 acetoxymethyl ester required the PE3 free acid as a starting material. The PE3 free acid was prepared by hydrolyzing the PE3 methyl ester using ten equivalents of KOH in a mixture of dioxane/methanol/water. The hydrolysis was monitored using Whatman MKC18F reverse phase plates developed with 50% methanol:water. Using this procedure, one can resolve the indicators at various stages of desterification. After hydrolysis, the solution was acidified with HCl to pH 2.0 which precipitates the PE3 free acid. The resulting precipitate was washed with $H_2O$ and then dried thoroughly under vacuum with PO5. Several solvents and conditions were tested to maximize yield and minimize quaternization of the piperazine amino nitrogen during the synthesis of the acetoxymethyl ester. The best results were obtained using freshly dried and distilled $CH_2C_{12}$ as the solvent and freshly dried and distilled ethyl diisopropyl amine (EDA) as the base. In a typical preparation, 2 mg of PE3 free acid was mixed with 100 mL $CH_2C_{12}$ followed by 100 mL acetoxymethyl bromide and 100 mL EDA. The formation of the ester was monitored on thin layer silica gel plates using 2% methanol in chloroform as solvent. When complete, the mixture was diluted into ethyl acetate and washed twice with aqueous $NaHCO_3$. The organic layer was then dried over $MgSO_4$ and the solvent was removed under vacuum. The PE3/AM was purified by silica gel column chromatography using 2% chloroform:methanol as the solvent. The yield was 1.5 mg or 75%.

EXAMPLES

Specific properties and embodiments of the present invention are outlined in the following examples. Such examples are for illustrative purposes only and are not intended to limit the scope of the claims in any way.

Example I

Spectral Properties

Absorbance and fluorescence properties for the new indicators disclosed herein, as exemplified by PE3 and FFP18 in the presence and absence of calcium are shown in Table 1. As expected, the absorbance, excitation, emission and quantum efficiency are all typical of fura-2. The calcium binding affinity of PE3 and FFP18 is somewhat weaker than that of fura-2. This represents an improvement when it comes to measuring cellular calcium levels because fura-2 is often used to measure calcium levels more than 1 log unit higher than its Kd.

TABLE 1

Physical Properties of PE3 and FFP 18

| DYE | Peak Absorption Wavelength (nm) | | Peak Emission Wavelength (nm) | | Calcium $K_d$ (nM) | | Magnesium Kd (mM) | | Fluorescence Quantum Efficiency | |
|---|---|---|---|---|---|---|---|---|---|---|
|  | Ca bound | Free anion | Ca bound | Free anion | 20° C. | 37° C. | 20° C. | 37° C. | Ca bound | Free anion |
| fura-PE3 | 335 | 364 | 495 | 508 | 204[c] | 209[a] | 4.3 | 4.0 | 0.27 | .043 |
| FFP 18 | 335 | 364 | 490 | 502 | 331 (551)[d] | 415[b] (400)[e] | 6.8 | 3.3 | 0.25 | 0.46 |

[a] 130 mM KCl, 20 mM NaCl, 1 mM free MgC12, 10 nM MOPS, pH 7.05, 37° C. Apparent Kd of CaEGTA used was 214 nM with an apparent Kd for MgEGTA of 8.96 mM.
[b] 130 mM KCl, 20 mM NaCl, 1 mM free MgC12, 10 nM MOPS, pH 6.9, 37° C. Apparent Kd of CaEGTA used was 423 nM with an apparent Kd for MgEGTA of 14.7 mM.
[c] 100 mM KCl, 10 mM MOPS, pH 7.3, 20° C. Apparent Kd of CaEGTA used was 95.4 nM.
[d] Indicator was adhered to liposomes and the washed pellet resuspended in 100 mM KCl, 10 mM HEPES, pH 7.2 and titrated at 20° C.
[e] Indicator was adhered to liposomes and the washed pellet resuspended in 100 mM KCl, 10 mM HEPES, pH 7.2 and titrated at 37° C.

Example 2 pH sensitivity

The calcium dissociation constant of BAPTA-like calcium chelators and indicators is strongly affected by electron withdrawing effects of substituents on the BAPTA aromatic rings. The zwitterionic indicators described herein each contain an ionizable amine. The difference in electron withdrawing effects of the ionized and unionized amine could potentially communicate to BAPTA, creating a situation were the calcium affinity varied with pH. The design of PE3 and FFP18 was aimed at minimizing or eliminating this possibility by insulating the ionizable amine from the BAPTA ring with an aliphatic spacer containing one or more carbons. To test the effectiveness of this design, the calcium Kd of PE3 and FFP18 was measured at different pH values and compared to the values obtained for fura-2. The values must be compared to those of fura-2 because fura-2 is already slightly pH sensitive to the presence of 2 aromatic amino groups. Thus, the aim of the test was to determine whether the piperazine amino group gives the indicator increased pH sensitivity. The results of the test show that the piperazine amino group causes little difference in pH sensitivity.

TABLE 2

Sensitivity relationship of PE3, FFP 18, and fura-2 to pH.

|  | pH 6.9 | pH 7.3 | DKd/pH |
|---|---|---|---|
| fura-2 | 216 +/− 4 | 161 +/− 2 | 55 |
| PE3 | 269 +/− 3 | 204 +/− 4 | 65 |
| FFP18 | 411 +/− 5 | 331 +/− 2 | 80 |

Titrations were carried out in 100 mM KCl, 10 mM MOPS at 20° C. and dissociation constants were determined assuming an apparent Kd for EGTA of 594 nM at pH 6.9 and 95.4 nM at pH 7. On page 36 of U.S. Pat. No. 4,603,209 (Tsien, et. al., 1987 Aug. 25), R2 is claimed as H, CH3, F, Cl, Br and C0–C4 alkoxy. The R2 of PE3 and FFP18 is none of these claimed in that patent.

Example 3

Example of loading PE3 into cells as an acetoxymethyl ester.

Fura-2 is commonly loaded into small cells by incubating cells with the fura-2 acetoxymethyl ester. The acetoxymethyl ester derivative is membrane permeant and subject to hydrolysis by intracellular esterases. When the esterases hydrolyze the acetoxymethyl esters, the 5 carboxyl groups are deprotected and the native indicator is regenerated. Since the acetoxymethyl ester does not bind calcium, the indicator will not respond to intracellular calcium transients unless the ester groups have been removed. To demonstrate that fura-PE3 can be loaded into cells as an acetoxymethyl ester derivative, 322 T lymphoma cells were incubated with 1 mM PE3 for 1 hour, washed and resuspended in HBSS containing 1% fetal bovine serum. An aliquot of this loaded cell suspension was then placed in a cuvette and the fluorescence was measured while alternating between 350 nm and 380 nm excitation FIG. 9. Baseline measurements were recorded for about 50 sec and then cells were stimulated with 50 mg/ml Concanavalin A ((FIG. 9 first arrow) which activated T cells by ligating the T cell antigen receptor which in turn stimulates a transient increase in intracellular calcium. The fluorescense response of PE3 to an increase in calcium is seen when Concanavalin A is added. Here the fluorescense at 340 nm increases indicating an increase in concentration of the calcium bound form of the indicator while the fluorescense at 380 nm decreases reflecting a decrease in concentration of the unbound form of the indicator. After cells had responded to Concanavalin, a calcium specific an ionomycin, was added (FIG. 9. second arrow) to elevate calcium further. This produces an even greater response of the indicator at 340 nm and 380 nm. Subsequently, cells were lysed with digitonin, a detergent which selectively lyses the plasma membrane of cells and releases the cytosolic indicator into the medium where calcium levels are high (1 mM) (FIG. 9. third arrow). This gives the maximum ratio of fluorescense at 340 nm/380 nm. Subsequently, EGTA was added to reduce free calcium levels to 10–9M. When calcium levels are reduced, fluorescense at 380 nm now becomes much brighter while the fluorescense at 340 becomes dim. (FIG. 9 fourth arrow).

Example 4

Leakage of indicator from 322 T lymphoma cells loaded with fura-2 or PE3.

The T cell lymphoma cell line was loaded with 1 mM fura-2/AM or 1 nM PE3/AM as for Example 3. Afterwards, an aliquot of dye loaded cells were placed in a cuvette and the fluorescense at 360 nm was recorded. Then 5 nM $Ni^{2+}$ was added to quench any indicator that was outside the cells.

The remainder of the loaded cell suspension was incubated for 1 hour at 37° C. Then a second aliquot was removed, placed in a cuvette together with 5 mM $Ni^{2+}$ and fluorescense recorded. The difference in fluorescense of $Ni^{2+}$ treated cells between 0 hour time point and the one hour time point represents indicator that leaked out of the cells into the extracellular medium over the 1 hour incubation period. FIG. 7.

Example 5

The intracellular distribution of FFP18 microinjected into smooth muscle cells.

The potassium salt of FFP18 was microinjected injected into individual smooth muscle cells. A fluorescence image of a smooth muscle cell was recorded before and after microinjection of FFP18. A graph indicating location of the calcium is shown in FIG. 11 while a single scan line is shown for a cross section of the muscle. As can be seen in FIG. 11A, after FFP18 is microinjected into the cells, the majority of the fluorescence is associated with the plasma membrane and nuclear membrane. Thus the majority of the calcium signal will be that which is in close proximity to the membranes where the indicator resides.

Example 6

Spectra obtained from FFP18 microinjected into cells shows that the fluorescence response to calcium is retained even when the indicator is bound to membranes.

Smooth muscle cells were microinjected with the FFP18 potassium salt, ionomycin was added to equilibrate calcium between the intracellular and extracellular environments and excitation spectra were recorded from a scanning microfluorometer as extracellular calcium levels were varied from 0 to 2000 mM. FIG. 12.

Example 7

FFP18 sees a larger calcium influx than fura-2

The amount of $Ca^{2+}$ entering the cell across the membrane was calculated by integrating the inward current signal and converting the charge to moles of $Ca^{2+}$ per cell volume. This $[Ca^{2+}]$ was divided by the average buffering capacity of these cells. The resulting smooth curve in FIG. 13 (A) represents an intracellular $[Ca^{2+}]$ curve due entirely to $Ca^{2+}$ influx across the plasma membrane without $Ca^{2+}$ re-uptake mechanisms in operation. The $[Ca^{2+}]$transients reported by the calcium indicators are shown by the more noisy traces FIG. 13 (A).

In 4 cells where the $[Ca^{2+}]$ transient was recorded using fura-2, the magnitude of the recorded and calculated increases in $[Ca^{2+}]$ were similar. The ratio of calcium influx measured using fura-2 to the calcium influx calculated from the integral of the current at the 200 msec time point gives a value of 0.9+/−0.05 [nM (recorded)/nM(calculated)]. An example of the data obtained from one of the 4 cells is shown in FIG. 13(A). In contrast, the increases in $[Ca^{2+}]$ recorded by FFP18 in 4 different cells was much larger than the calculated calcium transients giving a ratio of 2.6+/−1.0 [nM (recorded/nM (calculated)]. These results suggest that $[Ca^{2+}]$ rises much higher near the membrane where FFP18 is reporting calcium. FIG. 13(B).

Example 8

FFP18 sees a faster rate of calcium influx than fura-2.

Figure 14:
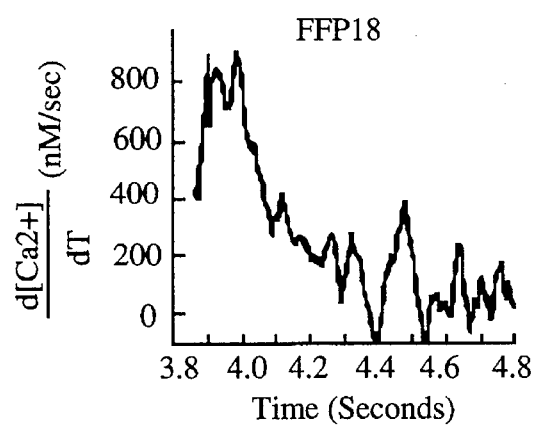
FIG. 14, 14A, 14B, and 14C are graphs showing time comparisons of changes in $Ca^{2+}$ for each of Fura-2 and FFP18, Example 8.
Figure 14B:
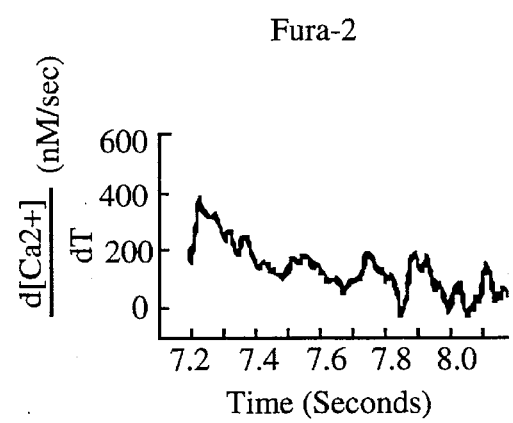
Figure 14A:
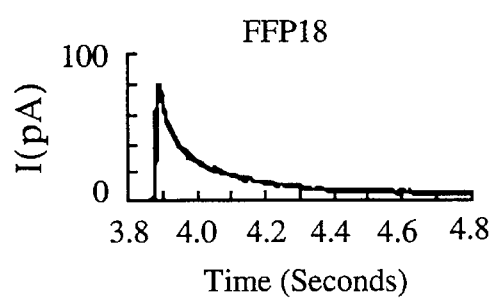
Figure 14C:
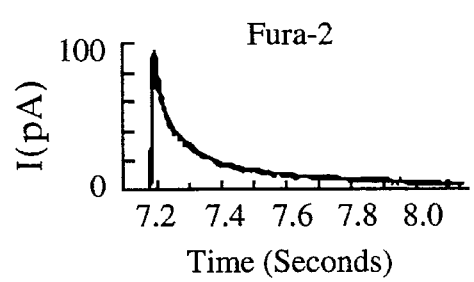

The change in calcium per unit time (DCa/DT) was determined for calcium transients measured either using FFP18 or fura-2 as the calcium indicator. While the magnitude of calcium current was the same for both cells when measured by an electrode, a greater signal was seen by FFP18. FIG. 14.

What is claimed is:

1. A class of cellular calcium indicators consisting of a) a chemical compound having the formula:

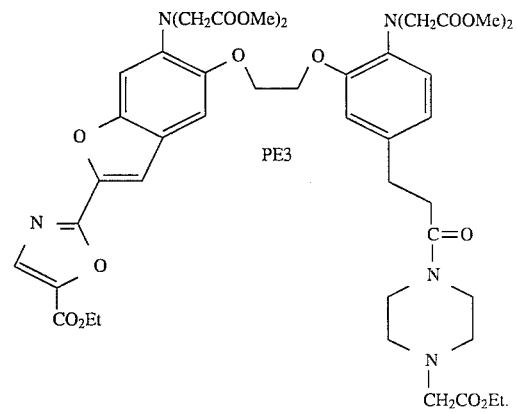

PE3 or b) a chemical compound having the formula:

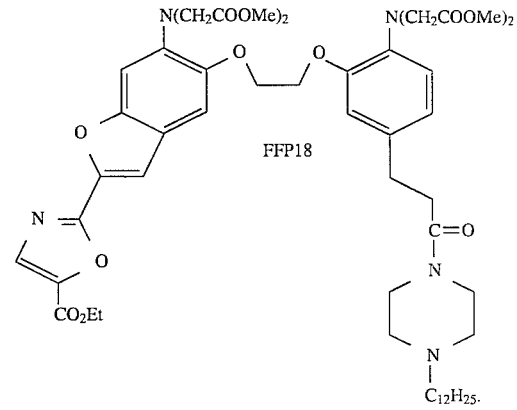

FFP18

2. A chemical compound having the following formula:
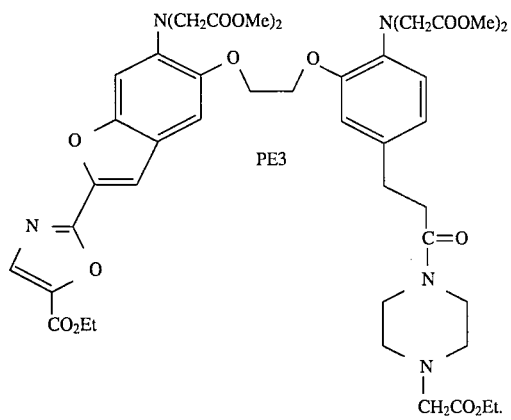
PE3
3. A chemical compound having the following formula
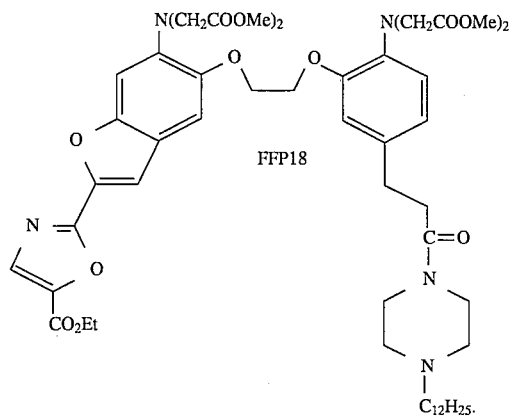
FFP18
* * * * *